United States Patent
Borrell et al.

(10) Patent No.: US 9,482,679 B2
(45) Date of Patent: Nov. 1, 2016

(54) COMPOSITION FOR USE AS AN ABNORMAL COAGULATION CONTROL PLASMA IN IN VITRO ASSAYS

(71) Applicant: GRIFOLS, S.A., Barcelona (ES)

(72) Inventors: Jose Segui Borrell, Barcelona (ES); Daniel Martorell Pena, Barcelona (ES)

(73) Assignee: GRIFOLS, S.A., Barcelona (ES)

( * ) Notice: Subject to any disclaimer, the term of this patent is extended or adjusted under 35 U.S.C. 154(b) by 0 days.

(21) Appl. No.: 14/656,362

(22) Filed: Mar. 12, 2015

(65) Prior Publication Data

US 2015/0260740 A1    Sep. 17, 2015

(30) Foreign Application Priority Data

Mar. 13, 2014 (ES) .................................. 201430343

(51) Int. Cl.
*G01N 33/96* (2006.01)

(52) U.S. Cl.
CPC ........... *G01N 33/96* (2013.01); *G01N 2496/05* (2013.01); *Y10T 436/106664* (2015.01)

(58) Field of Classification Search
CPC .............. G01N 2496/05; G01N 33/96; Y10T 436/106664
See application file for complete search history.

(56) References Cited

U.S. PATENT DOCUMENTS

2001/0004641 A1 *  6/2001  Hawkins ............... G01N 33/86
                                                              514/560

OTHER PUBLICATIONS

Wee, J. J. et al., "Identification of anticoagulant components in Korean Red Ginseng," Journal of Ginseng Research. vol. 34, No. 4, pp. 355-362, Dec. 2010.
Wang, S. et al., "The anticoagulant ability of ferulic acid and its applications for improving the blood compatibility of silk fibroin," Biomedical Materials, vol. 3, No. 4, 5 pp., Dec. 2008.
Lee, M.H. et al., "Tissue factor inhibitory sesquiterpene glycoside from Eriobotrya japonica," Archives of Pharmacal Research., vol. 27, No. 6, pp. 619-623, Jun. 2004.
Monien, B.H. et al., "Novel chemo-enzymatic oligomers of cinnamic acids as direct and indirect inhibitors of coagulation proteinases," Bioorganic & Medicinal Chemistry, vol. 14, No. 23, pp. 7988-7998, Dec. 2006.
Henry, B.L. et al., "Characterization of the plasma and blood anticoagulant potential of structurlaly and mechanistically novel oligomers of 4-hydroxycinnamic acids," Blood Coagulation & Fibrinolysis, vol. 20, No. 1, pp. 27-34, Jan. 2009.
Henry, B.L. et al., "Sulfated, low molecular weight lignins inhibit a select group of heparin-binding serine proteases," Biochemical and Biophysical Research Communications, vol. 417, No. 1, pp. 382-386, Jan. 2012.
Chang, Y.W., et al., "Platelet function analyzer (PFA-100(R)) offers higher sensitivity and specificity than thromboelastography (TEG(R)) in detection of platelet dysfunction," Acta Anaesthesiologica Taiwanica, vol. 47, No. 3, pp. 110-117, Sep. 2009.
Search Report dated Jun. 23, 2014 for ES201430343.

* cited by examiner

*Primary Examiner* — Paul Hyun
(74) *Attorney, Agent, or Firm* — Knobbe, Martens, Olson & Bear, LLP

(57) ABSTRACT

A composition, which relates to the field of the clinical analysis of blood, comprises human plasma, buffered isotonic solution and ferulic acid. The composition can be used as an abnormal coagulation control in haemostasis, coagulation and fibrinolysis assays. Ferulic acid can be used in the preparation of abnormal control plasma in haemostasis assays.

8 Claims, 12 Drawing Sheets

COMPOSITION FOR USE AS AN ABNORMAL COAGULATION CONTROL PLASMA IN IN VITRO ASSAYS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present invention relates to the field of the clinical analysis of blood, and in particular to a composition comprising human plasma, buffered isotonic solution and ferulic acid to be used as the abnormal coagulation control in haemostasis, coagulation and fibrinolysis assays. The present invention also relates to the use of ferulic acid in the preparation of abnormal control plasma in haemostasis assays.

2. Description of the Related Art

Haemostasis is the group of mechanisms which prevent animals that have a vascular system from bleeding out following an injury. The haemostasis mechanism has a variety of important functions: (a) keeping the blood in a fluid state when it flows through the vascular system, (b) stopping bleeding at the site of a wound or wherever there is blood loss, by forming a clot, and (c) ensuring the clot is removed once the wound has healed. Typically, five elements are involved in haemostasis, namely: the blood vessels, platelets (cell component), coagulation factors, coagulation inhibitors and the fibrinolytic system. Haemostasis thus involves a group of forces which have to interact in perfect balance—procoagulant forces and anticoagulant forces. This balance is controlled by various proteins, some of which are known as coagulation factors. It is a very delicate balance where any imbalance could lead to either a prothrombitic state or a blood disorder.

It is very important to precisely measure coagulation function because any impairment that is present could be life-threatening. This becomes particularly important in patients who undergo coagulation therapy in thromboembolic conditions.

The role of the haemostasis laboratory is to detect and recognise physiological changes in haematological and thrombotic diseases. To do so, various assays are used, such as primary haemostasis assays, coagulometric assays and immunological assays, which allow useful information to be obtained in order to help health professionals make a precise diagnosis and devise suitable treatment therefor.

Haemostasis assays can be divided into two distinct groups: initial haemostasis assessment, which can include the prothrombin time (PT), activated partial thromboplastin time (aPTT), determination of fibrinogen concentration, and thrombin time (TT); and the other group, which can include specific assays such as reptilase time (RT), activated coagulation time (ACT), and determination of the concentration of antithrombin (AT), protein C, protein S, von Willebrand factor, plasminogen and $\alpha 2$-antiplasmin (plasmin inhibitor).

In haemostasis laboratories, patient samples are analysed for a wide variety of haemostasis screens and specific assays throughout the working day. In these assays, methodological control of the variables that affect the efficiency and efficacy of the haemostasis assays is essential for a correct diagnosis.

The use of control plasmas plays an important role in these internal quality controls carried out by laboratories.

It is highly recommended to use, at regular intervals, one control in the normal coagulation time range and another in the abnormal range to ensure the proper functioning of the reagents and devices used in the haemostasis laboratory. Recommendations have been published regarding the frequency with which control materials should be tested for some coagulation assays. For example, the Clinical and Laboratory Standards Institute (CLSI) has published guidelines relating to the PT and aPTT assays. Said documents recommend testing, at least, two levels of control materials every 8 hours, or more frequently if samples are processed in a continuous manner as is the case in many laboratories. This document from the CLSI also indicates that the control sample should be used in the first assay that is carried out following a change of reagent or the inclusion of new reagents or following a significant apparatus change. The controls allow for the assessment of the analytical precision and deviation of both the coagulation assays in the coagulometer system employed and the reagents used.

Literature has been published relating to the preparation of coagulation control plasma, and some of these plasmas are currently commercially available. However, the majority of the methods described are time-consuming and include expensive steps for the absorption of critical plasma protein factors to obtain the abnormal coagulation properties. One method for preparing abnormal coagulation control plasma comprises incubating normal plasma with aluminium hydroxide and then centrifuging said plasma. The sediment contains various coagulation factors and the resultant supernatant can be used as pathological control plasma. Abnormal clotting times are achieved by removing the coagulation factors from the plasma. However, the coagulation control plasma thus obtained is not completely satisfactory, since abnormal results are obtained in some assays whilst in others, for example factors VIII, XI and XII, as well as in other haemostasis assays such as TT and RT, the activity is within the normal range.

Another method for producing an abnormal coagulation control is to dilute normal plasma. Said method is described in an international guide (NCCLS H30-A2), which mentions how to prepare an abnormal control plasma for determining fibrinogen according to the Clauss method. Said document also describes how a series of normal plasmas can be diluted with a barbital buffer to obtain plasma having an abnormal result (low fibrinogen content). The final result of the dilution of a series of normal plasmas is abnormal in the majority of the haemostasis assays. However, said coagulation control plasma is not abnormal for TT and RT for example. The same result is obtained by diluting the normal plasma with other solutions, such as a 4% albumin solution.

SUMMARY OF THE INVENTION

The present invention discloses an abnormal coagulation control plasma that overcomes all the aforementioned drawbacks. The abnormal control plasma of the present invention ensures both results in the abnormal range in a large number of haemostasis assays, including TT and RT, and determination of the activity of specific coagulation factors. The present inventors have surprisingly found that by adding ferulic acid in an isotonic solution to normal plasma, it is possible to obtain an abnormal control plasma that can be used effectively in the majority of haemostasis assays.

Without being linked to any theory in particular, it is possible that this property of the ferulic acid is obtained by means of a characteristic anticoagulant property thereof. However, the fact that a substance has anticoagulant properties does not mean that it is suitable for producing abnormal plasma. For example, warfarin is one of the most widely used anticoagulants in healthcare for treating patients at risk of thrombosis, and has been used as a medication for more than 50 years. However, this compound is not suitable for being added to plasma and producing an abnormal coagulation control since its mechanism of action is based on inhibiting the synthesis of coagulation factors that depend on vitamin K. As an anticoagulant, warfarin requires a complete in vitro system.

Other anticoagulant compounds, such as heparin or ethylenediaminetetraacetic acid (EDTA), can indeed be added to normal plasma and produce abnormal times in the haemostasis assays. However, the present inventors have not obtained similar results with the anticoagulants heparin or EDTA. Neither of these anticoagulants is suitable for producing abnormal plasma since they have inconsistent effects on haemostasis assays. That is to say, the optimum concentration for obtaining an abnormal time in an assay is insufficient or excessive for another assay. For example, heparin prolongs the aPTT assay, yet does not affect the PT assay, or does so to a lesser extent. Moreover, heparin does not prolong the RT assay, or rather does not produce abnormal plasma for RT. The case is similar with EDTA, which, at a certain concentration, can prolong the RT assay, yet does not affect the results of PT, aPTT and TT assays, or does so very slightly.

Therefore, the present invention discloses a composition comprising ferulic acid, buffered isotonic solution and human plasma for use as an abnormal coagulation control plasma in haemostasis assays.

In the composition of the present invention, the term 'human plasma' refers to the liquid part of the blood from which the red blood cells, white cells and platelets have been removed. In addition, the human plasma used in the composition of the present invention is one which has a normal coagulation time in the various assays and is thus capable of being used as a normal control in coagulation assays. Said plasma can be obtained by any methods known in the art, for example by plasmapheresis.

An additional advantage of the composition of the present invention for abnormal coagulation control in haemostasis assays is that said composition can be frozen or lyophilised and remains stable once thawed or reconstituted.

To obtain a composition for abnormal coagulation control in haemostasis assays, it is preferable to use a pool of normal plasma containing plasma from two or more healthy human donors. Said plasma pool can be prepared by gentle mixing in a suitable container. The concentration of normal plasma in the composition of the present invention is in the range of from 15% v/v to 75% v/v.

The main role of the buffered isotonic solution present in the composition of the present invention for abnormal coagulation control in haemostasis assays is that of maintaining a pH around the physiological pH, i.e. between 6.5 and 8.5, but also to allow the plasma to be diluted so as to obtain an abnormal coagulation time, when combined with ferulic acid. The isotonic solution of the present invention can be any isotonic solution known in the art. Preferably, the isotonic solution of the present invention is a buffer that maintains a pH around the value of the physiological pH between 6.5 and 8.5 (for example Tris, HEPES, MOPS or CHAPS). The amount of isotonic solution in the composition of the present invention is in the range of from 40% v/v to 70% v/v.

On the other hand, the amount of ferulic acid in the composition of the present invention is in the range of approximately 0.01% w/v to approximately 1% w/v.

In addition, the composition of the present invention for abnormal coagulation control in haemostasis assays can optionally comprise a coagulation factor stabiliser. A coagulation factor stabiliser can provide said composition with additional stability. Said coagulation factor stabiliser is preferably glycine, more preferably, said glycine is present in the composition for abnormal coagulation control in haemostasis assays of the present invention in an amount of from approximately 0.1% w/v to approximately 4% w/v.

The composition of the present invention for abnormal coagulation control in haemostasis assays can also optionally comprise a protein stabiliser or a protein additive and/or a bulking agent, and a preservative. The main function of said stabiliser is to preserve the functionality of the proteins once they have been lyophilised. Said stabiliser can be any stabiliser known by a person skilled in the art.

Finally, the present invention discloses the use of ferulic acid in the preparation of an abnormal coagulation control in haemostasis assays.

DETAILED DESCRIPTION OF CERTAIN EMBODIMENTS

Examples

Example 1

Preparation of Abnormal Plasma Control Compositions for Haemostasis Assays

To assess the effect of different anticoagulants in various haemostasis assays, different plasma compositions were prepared. Use was made of citrated normal human plasma (16 mM of citrate), stored at a temperature of below −70° C. and thawed in a bath at 37° C. HEPES was then added up to a final concentration of 40 mM and the pH was adjusted to between 7.4 and 7.6 using NaOH 1N. Various plasma compositions were prepared. No anticoagulant was added to the first composition, which was used as a control. Increasing concentrations of the anticoagulants being analysed were added to the others: ferulic acid (0.5%, 1% and 1.5%), heparin (0.1 IU/mL, 0.5 IU/mL and 1 IU/mL) and EDTA (0.5 mg/mL, 1 mg/mL, 1.5 mg/mL). Each plasma composition was analysed for the aforementioned PT, aPTT, TT and RT assays in a Q Haemostasis Analyzer (Diagnostic Grifols, Spain) using the reagents DG-PT, DG-APTT Synth, DG-TT L Human and GD-Fibroclotin of Diagnostic Grifols.

Example 2

Effect of Compositions Comprising Anticoagulants in the PT Assay

Figure 1:
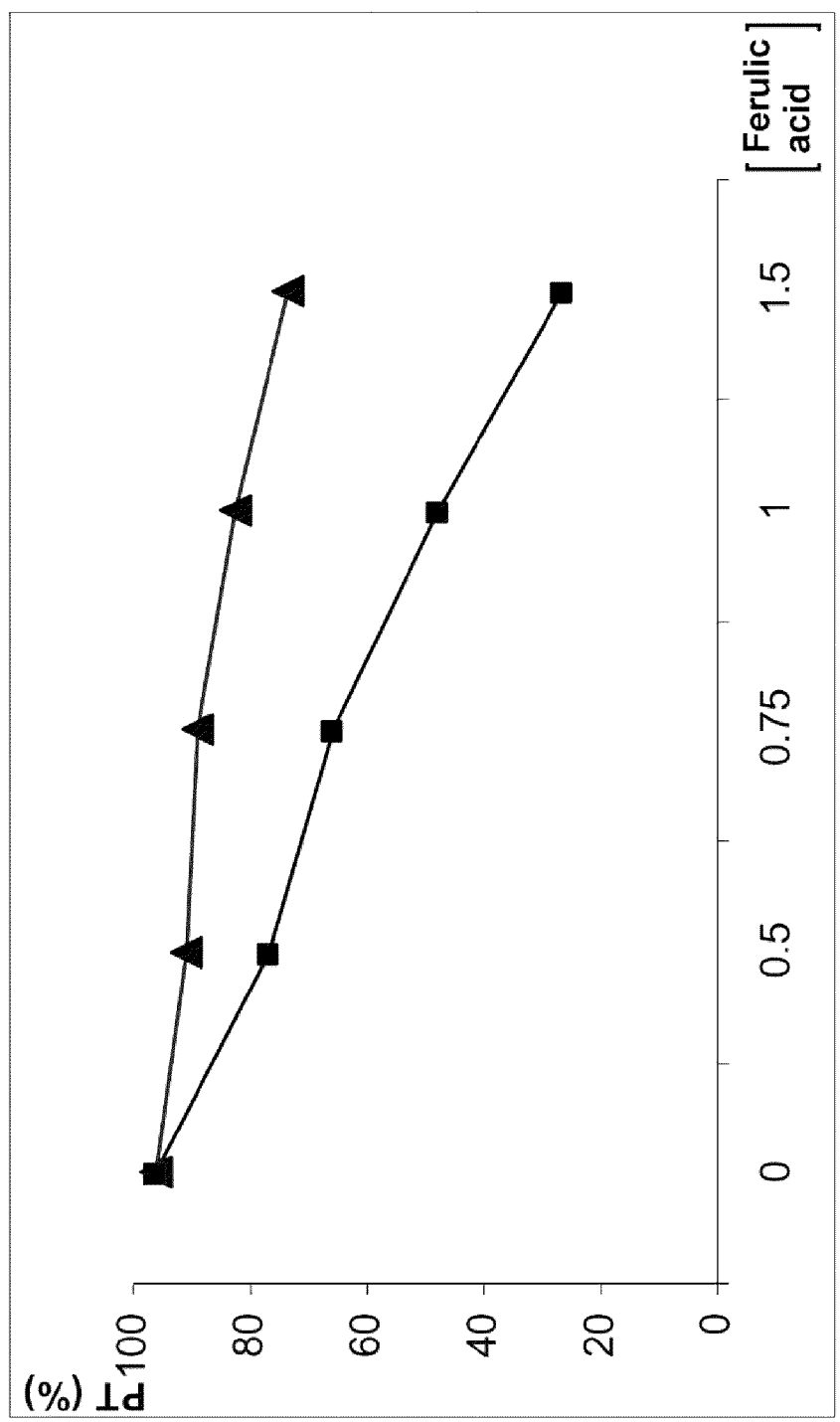
FIG. 1 shows the effect of ferulic acid with respect to control samples in the PT haemostasis assay.
Figure 2:
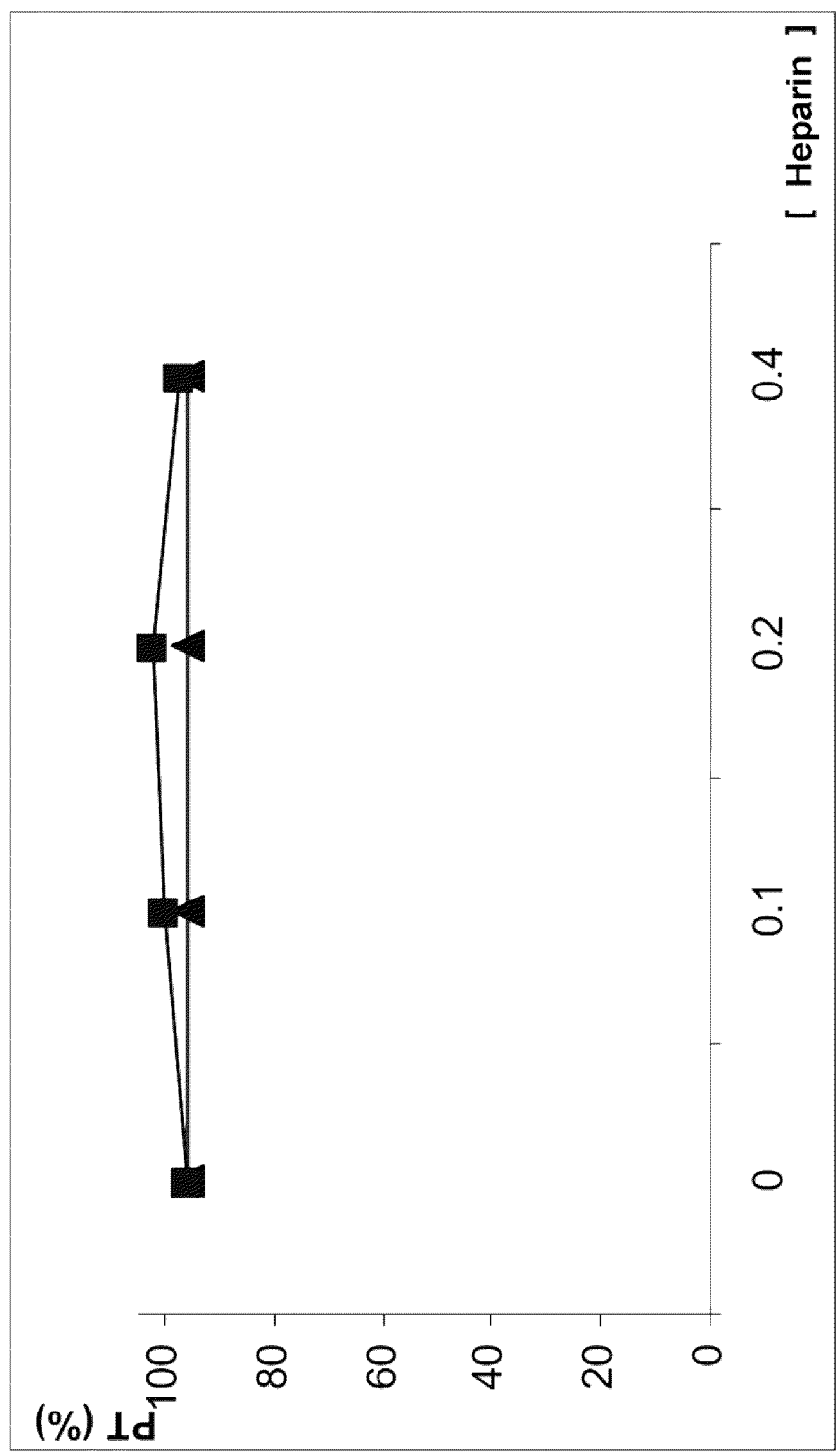
FIG. 2 shows the effect of heparin with respect to control samples in the PT haemostasis assay.
Figure 3:
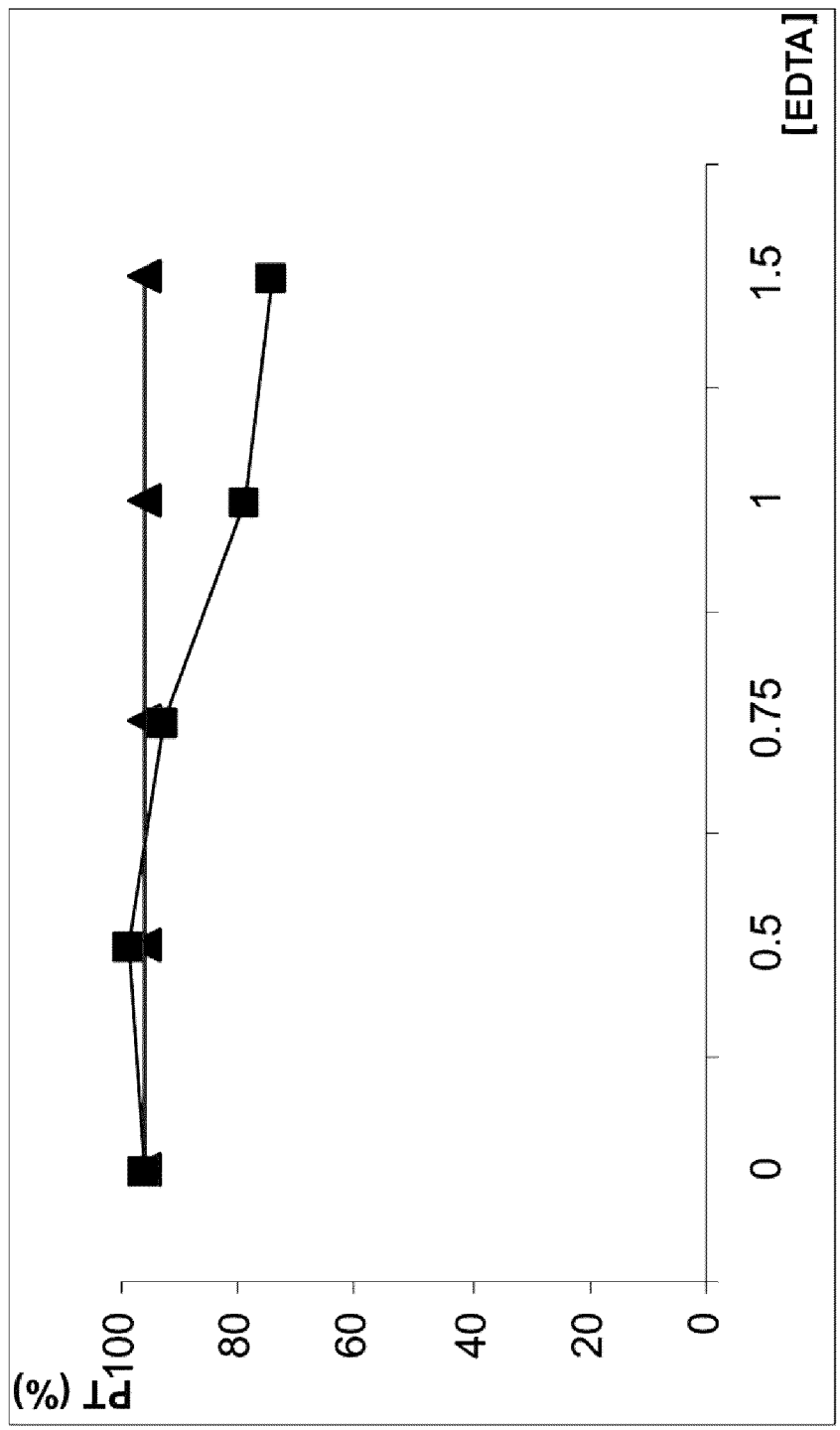
FIG. 3 shows the effect of EDTA with respect to control samples in the PT haemostasis assay.

FIG. 1-3 show the results obtained in the PT assay with the various anticoagulants and plot the time obtained in the PT assay as a function of the concentration of the anticoagulant present in the plasma. The control (plasma having no anticoagulant) is shown by triangles and the compositions comprising ferulic acid, heparin and EDTA are shown by squares. It can be seen that ferulic acid (FIG. 1) and EDTA (FIG. 3) produce a reduction in the percentage of PT activity that is proportional to the amount of anticoagulant present in the plasma. By contrast, heparin (FIG. 2) does not cause any different result to that of the plasma having no anticoagulant. This means that, at the concentrations tested, heparin has no effect on the PT assay. On the other hand, ferulic acid and EDTA added to normal plasma do produce a reduction in the percentage of PT activity.

Example 3

Effect of Compositions Comprising Anticoagulants in the aPTT Assay

Figure 4:
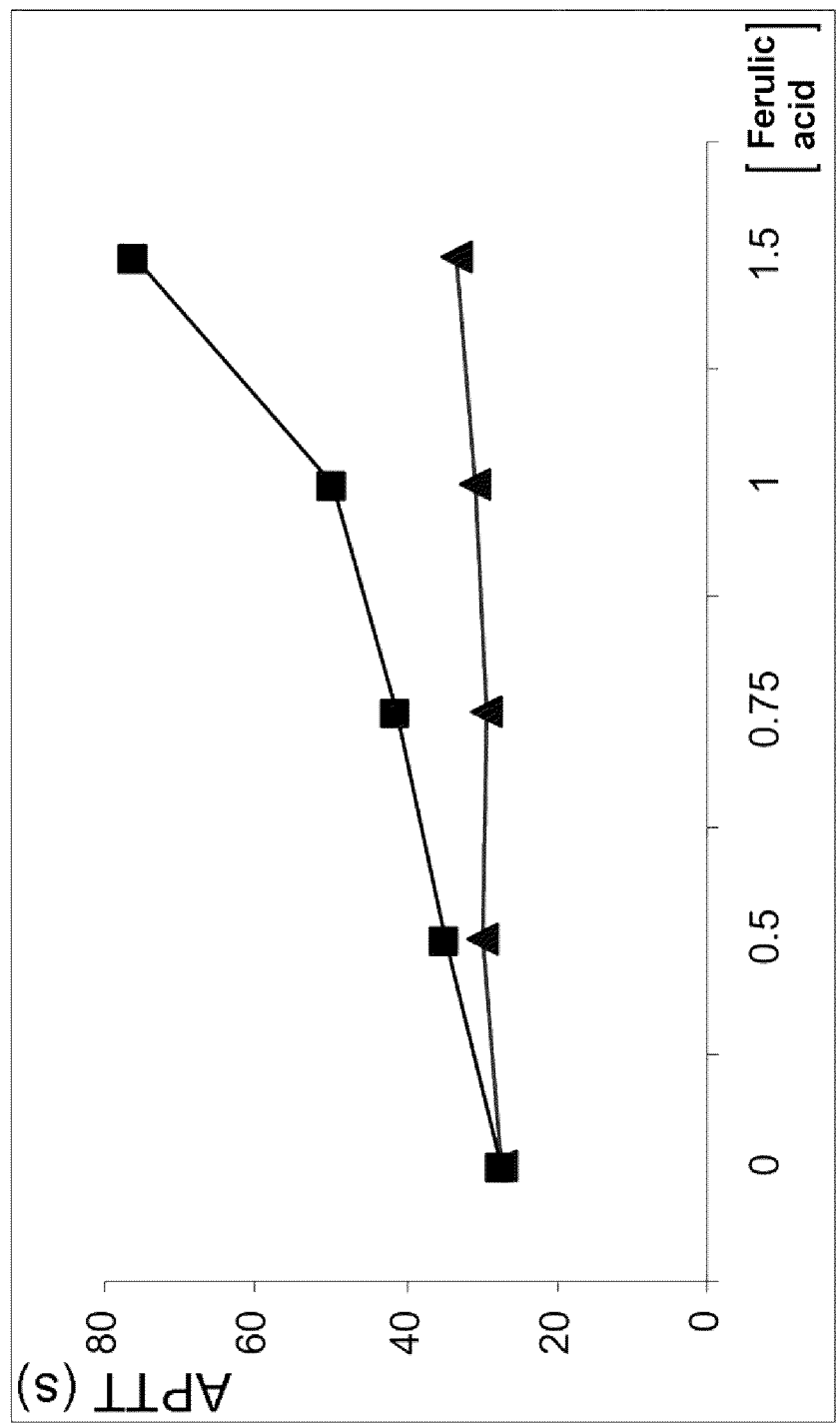
FIG. 4 shows the effect of ferulic acid with respect to control samples in the aPTT haemostasis assay.
Figure 5:
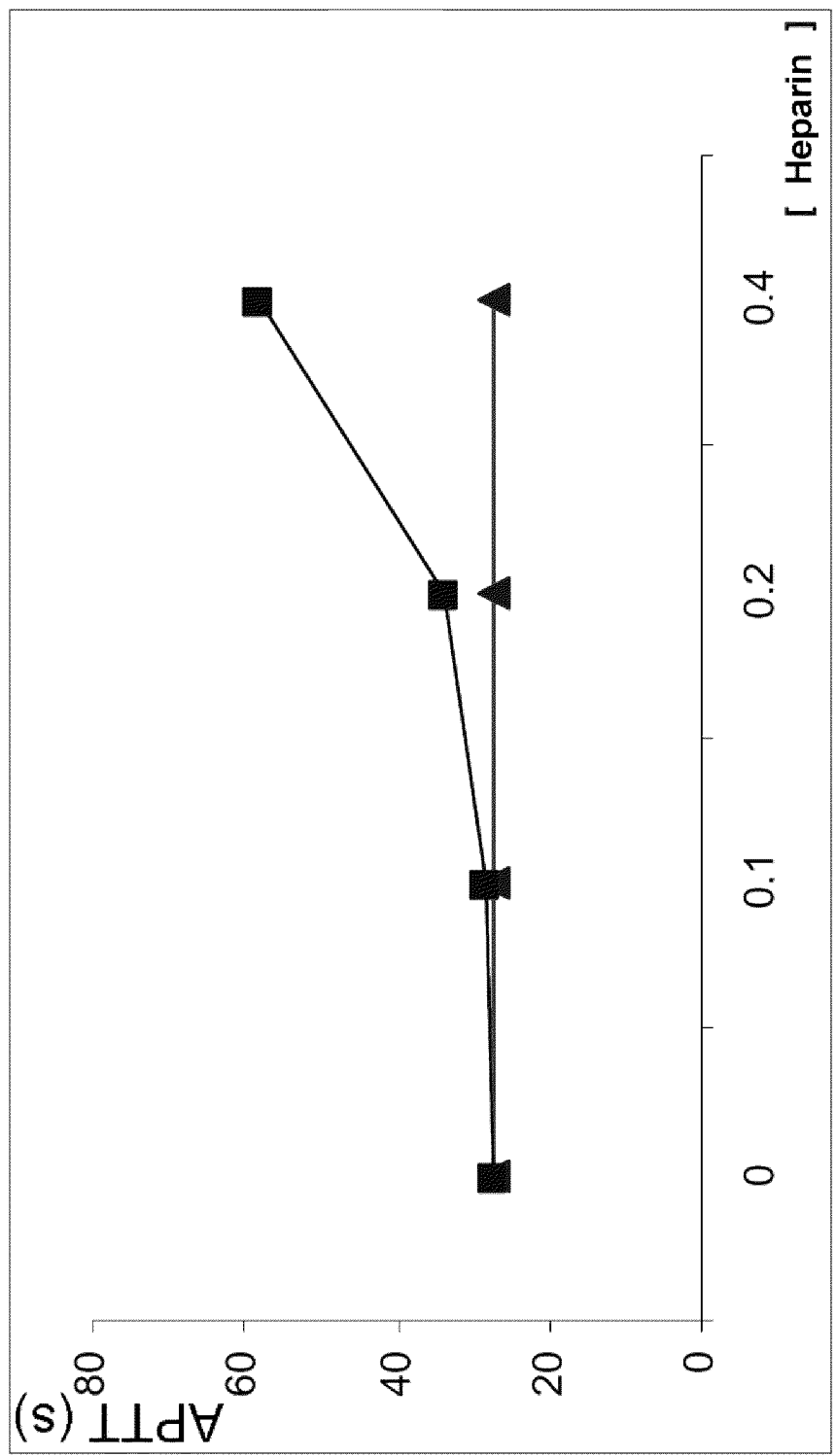
FIG. 5 shows the effect of heparin with respect to control samples in the aPTT haemostasis assay.
Figure 6:
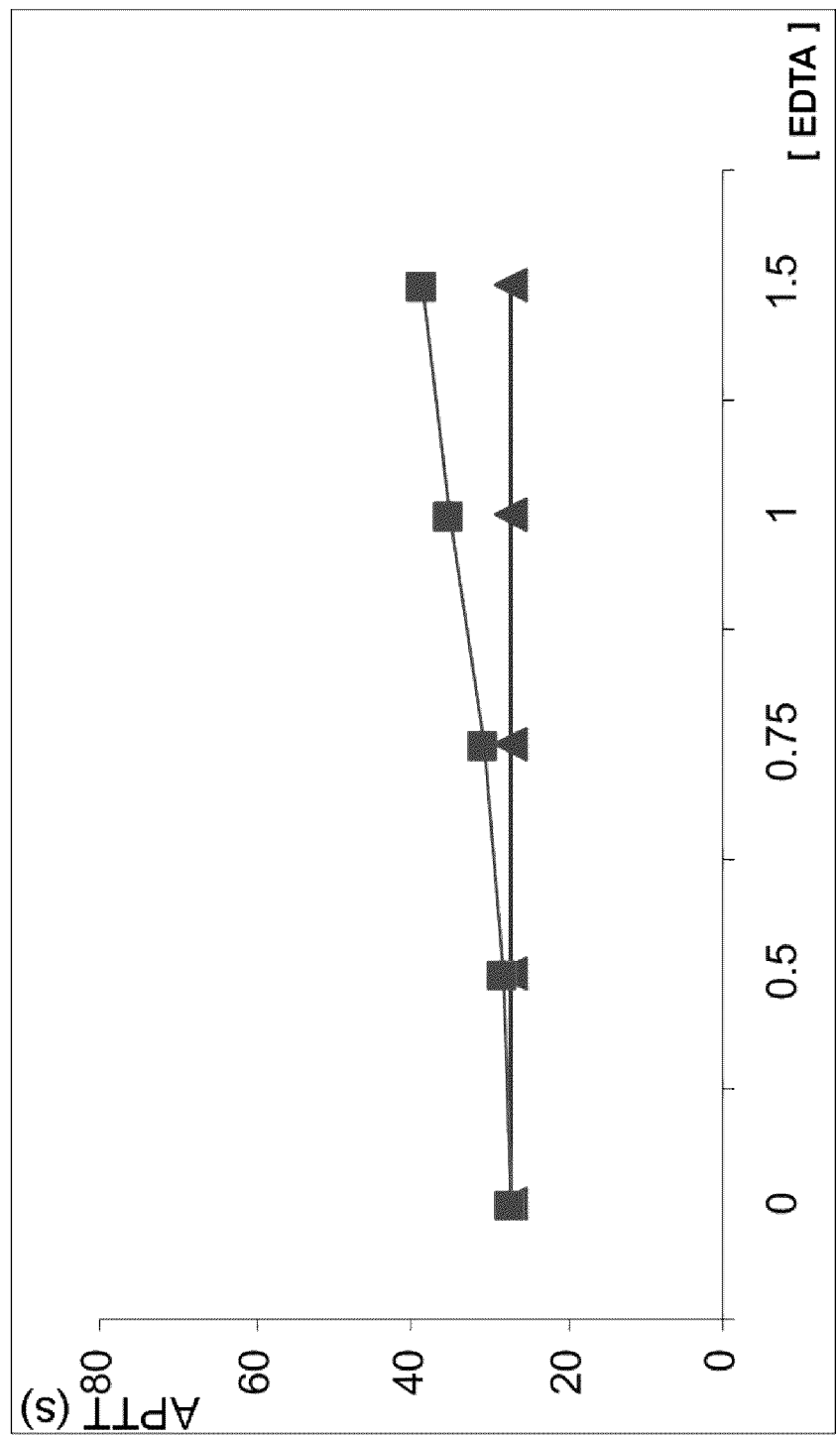
FIG. 6 shows the effect of EDTA with respect to control samples in the aPTT haemostasis assay.

The same plasmas prepared in Example 1 were tested in the aPTT assay (FIG. 4-6). In this assay, all the anticoagulants added to the plasma, i.e. ferulic acid (FIG. 4), heparin (FIG. 5) and EDTA (FIG. 6) prolong the PT assay. In addition, the prolongation in the result of the assay is proportional to the amount of anticoagulant present in the plasma.

Example 4

Effect of Compositions Comprising Anticoagulants in the TT Assay

Figure 7:
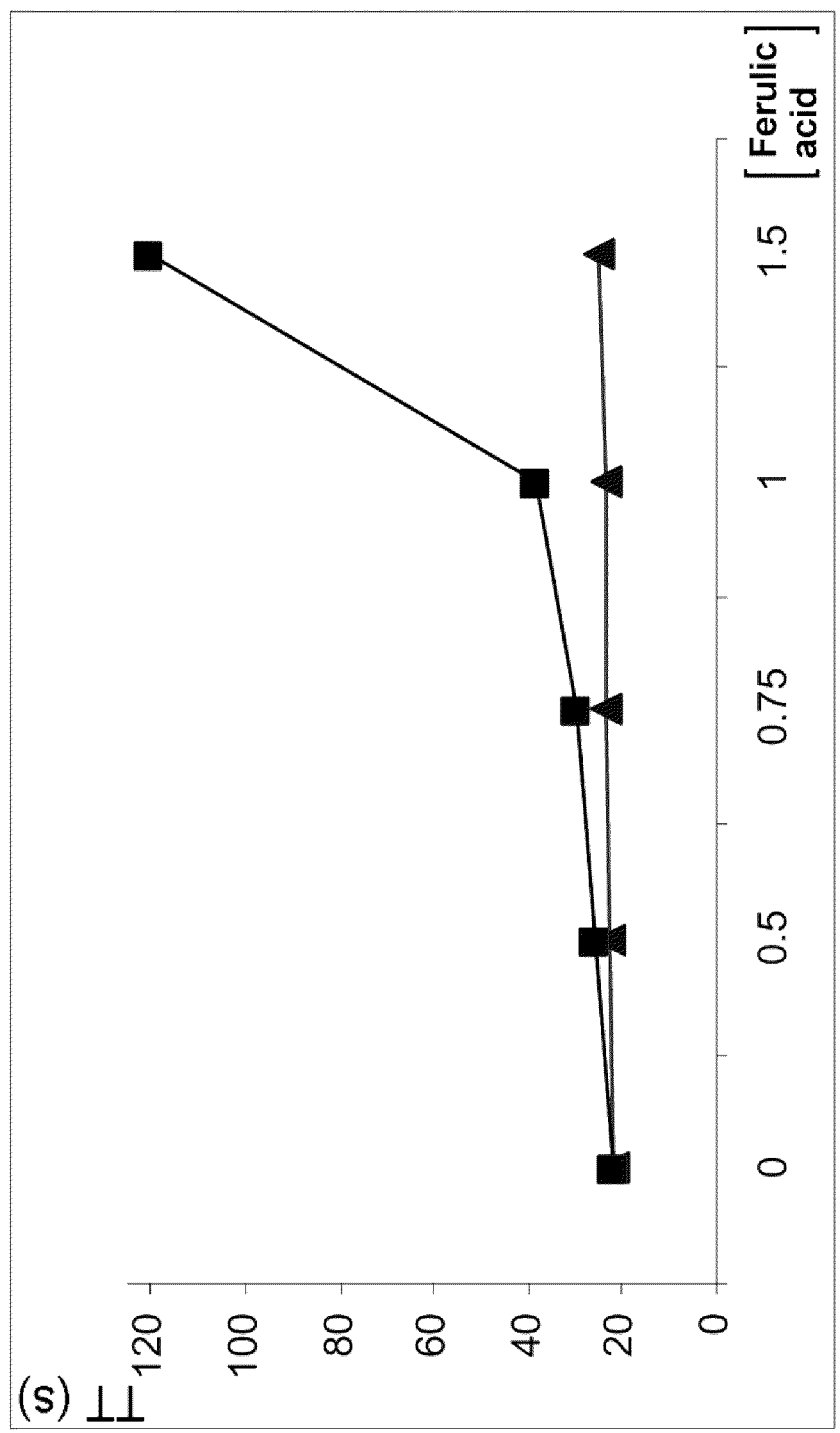
FIG. 7 shows the effect of ferulic acid with respect to control samples in the TT haemostasis assay.
Figure 8:
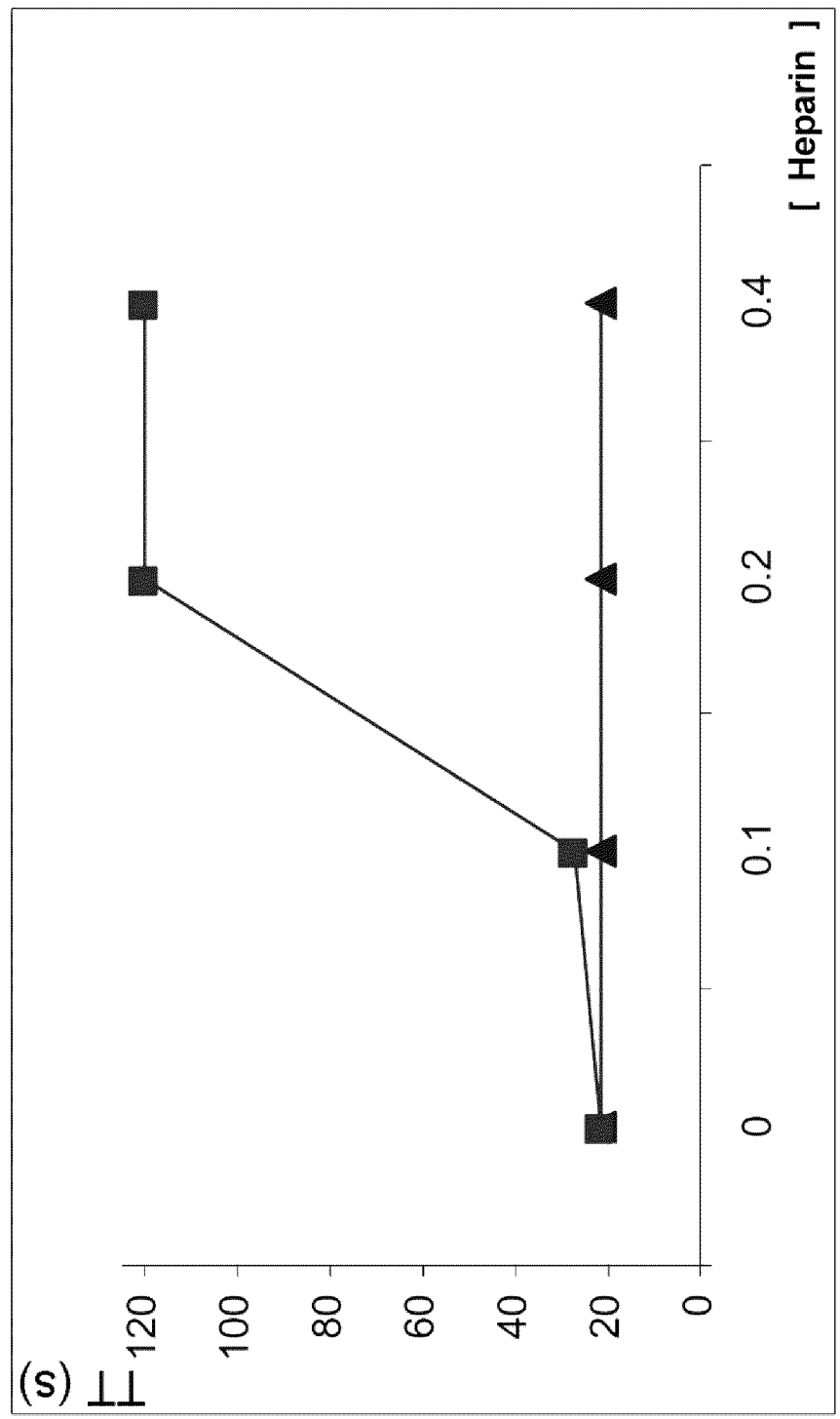
FIG. 8 shows the effect of heparin with respect to control samples in the TT haemostasis assay.
Figure 9:
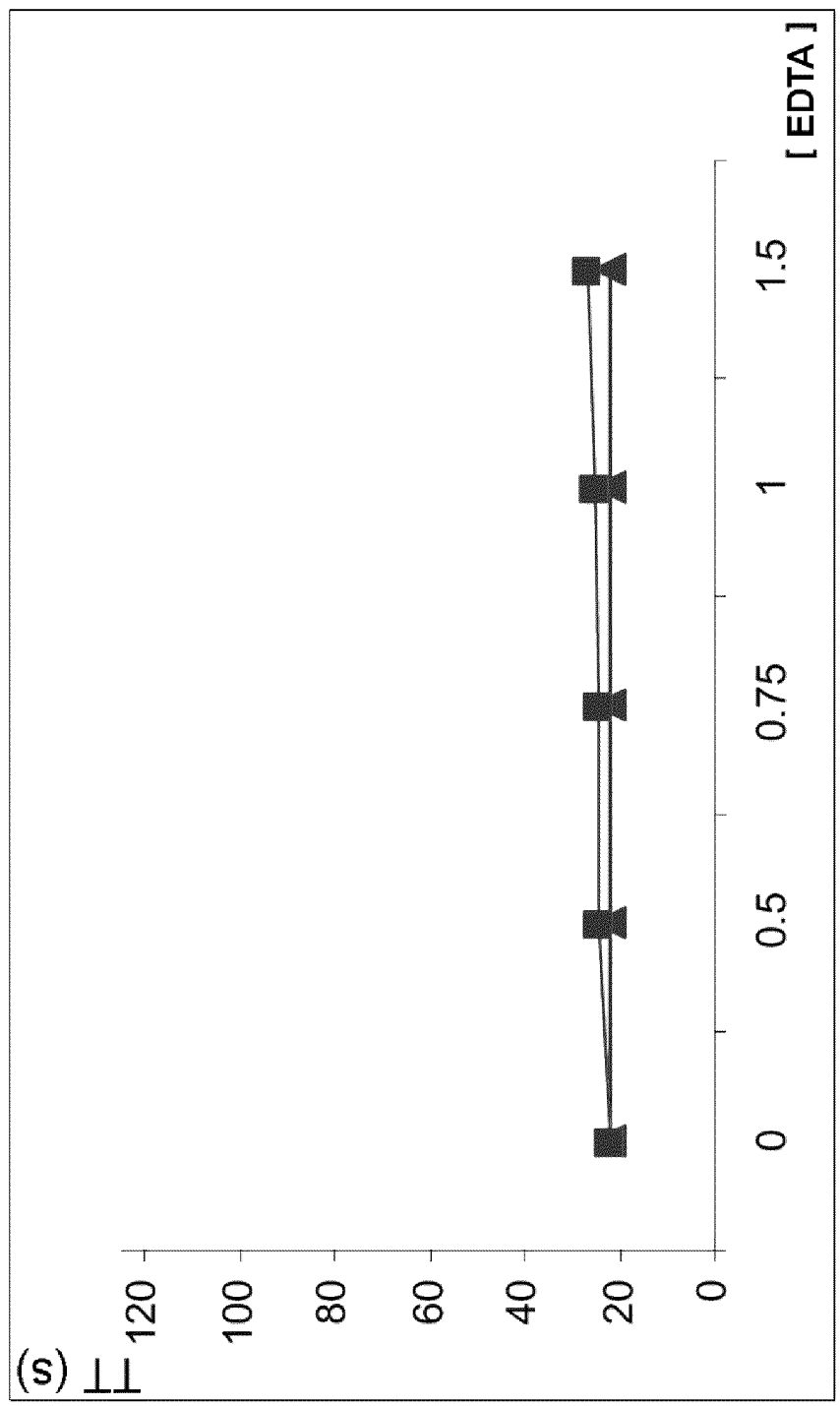
FIG. 9 shows the effect of EDTA with respect to control samples in the TT haemostasis assay.

The same plasmas prepared in Example 1 were tested in the TT assay. FIG. 7-9 show the TT results obtained when testing the prepared plasmas. Of the three anticoagulants analysed, EDTA (FIG. 9) does not prolong the result of the assay, that is to say, does not generate an abnormal TT. By contrast, both heparin (FIG. 8) and ferulic acid (FIG. 7) do produce an abnormal TT.

Example 5

Effect of Compositions Comprising Anticoagulants in the RT Assay

Figure 10:
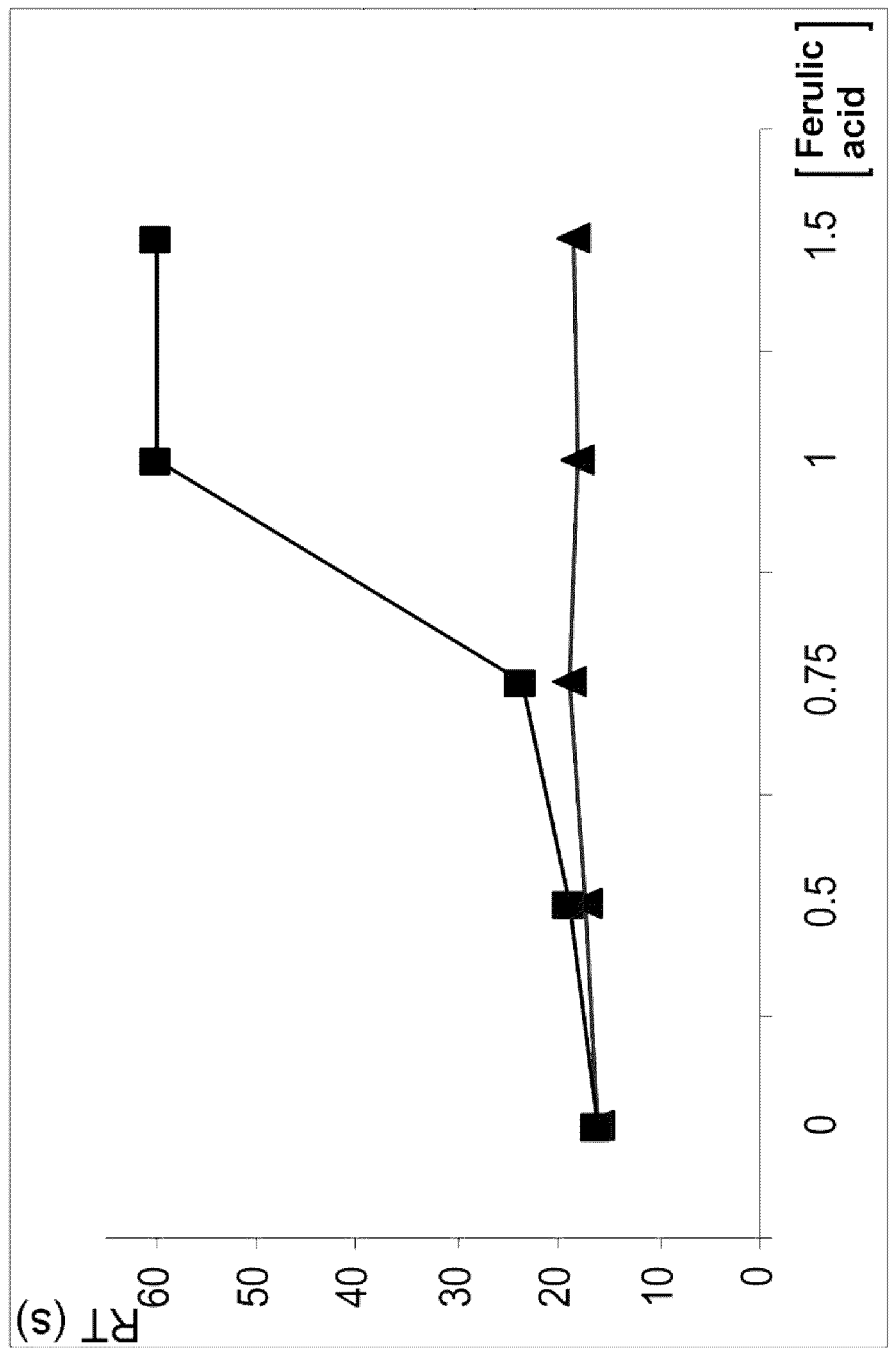
FIG. 10 shows the effect of ferulic acid with respect to control samples in the RT haemostasis assay.
Figure 11:
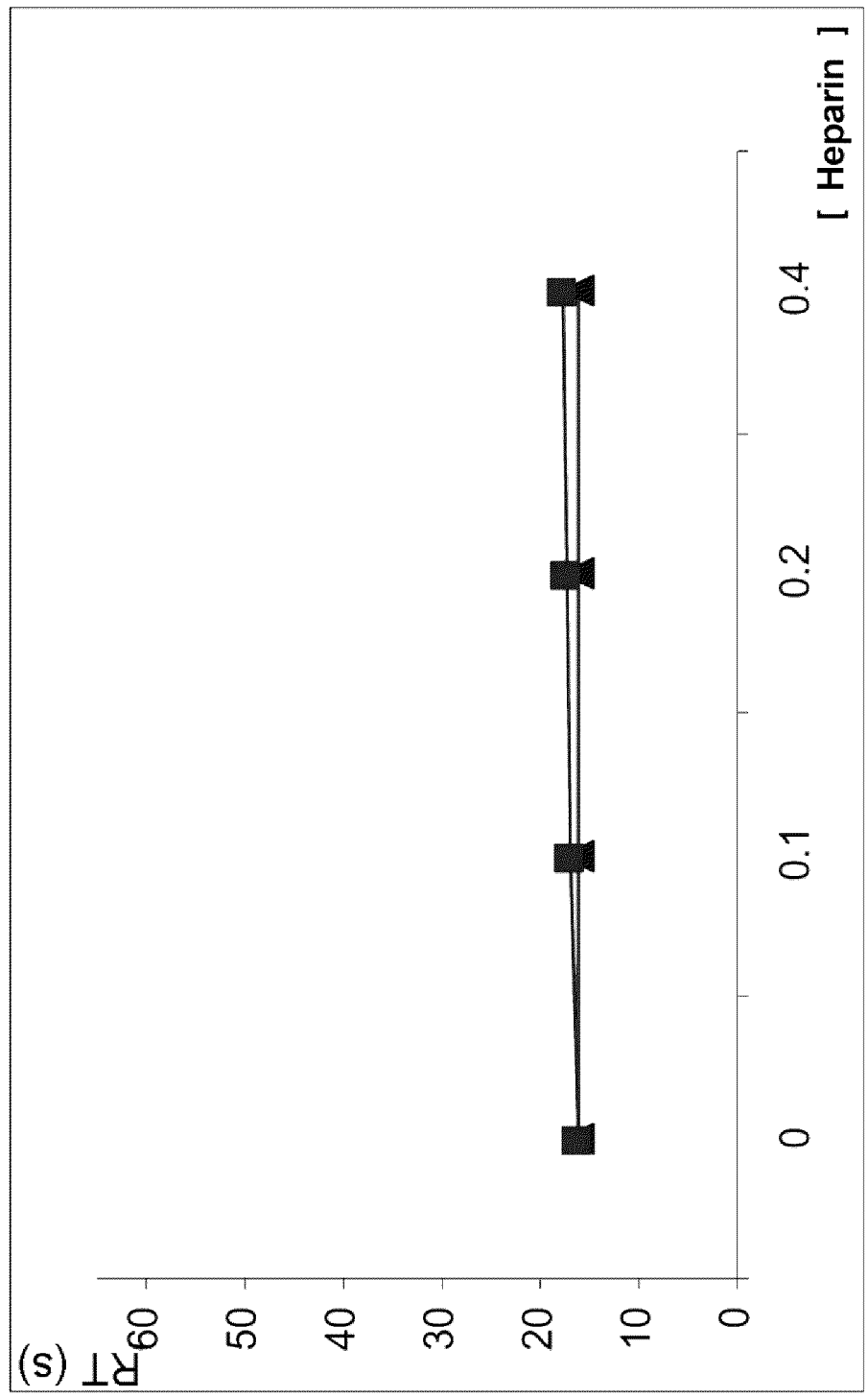
FIG. 11 shows the effect of heparin with respect to control samples in the RT haemostasis assay.
Figure 12:
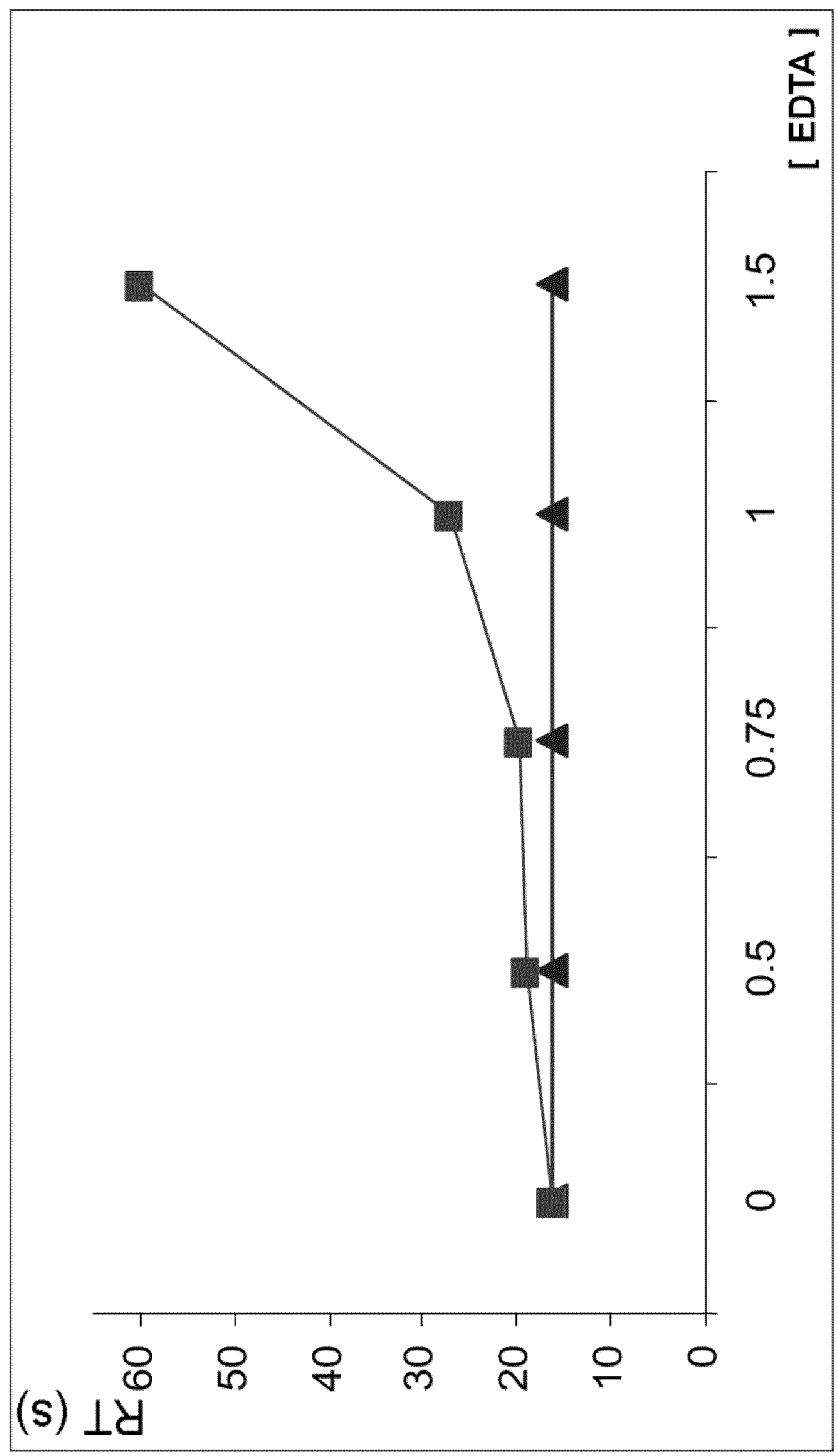
FIG. 12 shows the effect of EDTA with respect to control samples in the RT haemostasis assay.

The same plasmas prepared in Example 1 were tested in the RT assay. Referring to the results of the RT assay (FIG. 10-12), the only anticoagulant that does not produce an abnormal result after being added to a normal plasma pool is heparin (FIG. 11). Heparin does not prolong the RT at any of the concentrations tested. Plasmas containing the anticoagulants ferulic acid (FIG. 10) and EDTA (FIG. 12) do produce an abnormal RT result.

On the basis of the results shown in the examples and the preceding figures, the anticoagulant power of ferulic acid and its ability to cause abnormal results in all haemostasis assays after being added to normal plasma are clear. In addition, ferulic acid prolongs the assays in a balanced manner, thus making it suitable for the production of abnormal control plasma.

Although the invention has been described with respect to preferred embodiments, these should not be considered to be limiting to the invention, which will be defined by the broader interpretation of the following claims.

What is claimed is:

1. A composition for use as an abnormal coagulation control plasma in in vitro assays, comprising human plasma, buffered isotonic solution and ferulic acid, wherein said buffered isotonic solution has a pH of between 6.5 and 8.5, and an amount of the ferulic acid is in the range of 1% w/v to 1.5% w/v.

2. The composition according to claim 1, wherein the human plasma is a plasma pool comprising plasma from two or more healthy human donors.

3. The composition according to claim 1, wherein a concentration of the human plasma is in the range of 15% v/v to 75% v/v.

4. The composition according to claim 1, wherein an amount of said isotonic solution is in the range of 40% v/v to 70% v/v.

5. The composition according to claim 1, wherein the composition further comprises a coagulant factor stabilizer.

6. The composition according to claim 5, wherein the coagulation factor stabilizer comprises glycine.

7. The composition according to claim 6, wherein the glycine is present in said composition in an amount of 0.1% w/v to 4% w/v.

8. The composition according to claim 1, wherein the composition further comprises a protein stabilizer and a preservative.

* * * * *